United States Patent [19]

Vincent et al.

[11] 4,027,028

[45] May 31, 1977

[54] ARYLETHERS AND PHARMACEUTICAL COMPOSITIONS

[75] Inventors: Michel Vincent, Bagneux; Georges Remond, Versailles; Michel Laubie, Vaucresson, all of France

[73] Assignee: Science Union et Cie, France

[22] Filed: Nov. 10, 1975

[21] Appl. No.: 630,145

[52] U.S. Cl. .......................... 424/267; 260/293.77; 260/293.58; 260/293.75

[51] Int. Cl.² ...................................... C07D 211/58

[58] Field of Search ............... 260/293.77, 293.58; 424/267

[56] References Cited

UNITED STATES PATENTS

| | | | |
|---|---|---|---|
| 3,869,463 | 3/1975 | Archibald | 260/293.77 |
| 3,910,931 | 10/1975 | Cavalla et al. | 260/293.77 |

FOREIGN PATENTS OR APPLICATIONS

| | | | |
|---|---|---|---|
| 2,429M | 3/1964 | France | |
| 2,430M | 3/1964 | France | |
| 2,431M | 3/1964 | France | |
| 1,393,979 | 12/1973 | United Kingdom | 260/293.76 |
| 1,345,872 | 8/1971 | United Kingdom | 260/293.77 |

*Primary Examiner*—Norma S. Milestone
*Attorney, Agent, or Firm*—Gordon W. Hueschen

[57] ABSTRACT

This invention relates to amino piperidines bearing on the endocyclic nitrogen atom an aryloxy alkyl side chain and the acid addition salts thereof. This invention also relates to processes for making the same.

The compounds of this invention have therapeutical utility namely in the cardiovascular field. They may be used in the form of pharmaceutical compositions.

14 Claims, No Drawings

ARYLETHERS AND PHARMACEUTICAL COMPOSITIONS

DESCRIPTION OF THE PRIOR ART

The prior art may be illustrated with the following references

French drug Patents Nos. 2429 M; 2430 M; 2431 M; Belgian Patent No. 615,350.

SUMMARY OF THE INVENTION

This invention relates to new 4-amino piperidines and more particularly to N-aralkoxy 4-phenylamino piperidines. The aryl and phenyl nuclei may be unsubstituted or substituted by one or several substituents.

This invention also provides processes for producing such compounds. Namely they may be produced by condensing an aryloxy alkyl halide with a 4-phenylamino piperidine.

This invention also relates to pharmaceutical compositions including as active ingredient at least one 4-phenylamino N-aryloxy alkyl piperidine or an acid addition salt thereof in admixture with an inert carrier.

This invention further relates to a method for treating hypertension in hypertensive humans or animals

DESCRIPTION OF THE PREFERRED EMBODIMENTS

The present invention relates to novel arylethers, to the processes for their preparation and to pharmaceutical compositions incorporating them as active ingredient.

More particularly the present invention provides aryloxy lower alkyl piperidines of the general formula I:

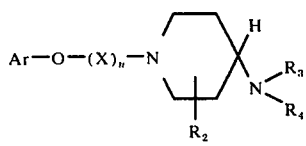

(1)

in which $R_2$ is a hydrogen or a lower alkyl radical $R_3$ is the acyl residue of an organic alkylcarboxylic acid having up to 10 carbon atoms.

$R_4$ is a phenyl radical selected from the group consisting of unsubstituted phenyl and a substituted phenyl radical of the formula

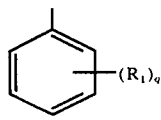

wherein $R_1$ is a radical selected from the group consisting of halogen, lower alkoxy and lower alkylene dioxy and $q$ is an integer of 1 to 3 with the proviso that when $R_1$ is a lower alkylene dioxy, $q$ is 1 or 2, X is an alkylene radical selected from the group consisting of

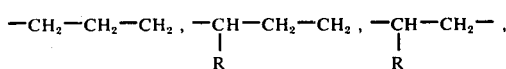

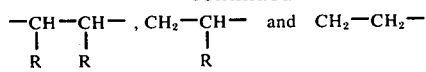

in which

R is a lower alkyl radical $n$ is 1 or 2 and Ar is an aromatic homo-or hetero cyclic radical selected from the group consisting of a. a phenyl radical of the general formula

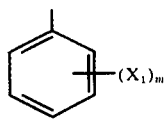

in which $X_1$ is a radical selected from the group consisting of halogen atom, lower alkyl, lower alkenyloxy, lower alkynyloxy, lower alkylthio, carboxyl, lower alkoxy carbonyl, lower alkenyl, lower alkylene-dioxy, nitro, amino, lower alkylamino, di(lower alkyl) amino, lower acylamino, sulfamido, lower alkylamino sulfonyl, di(lower alkylamino) sulfonyl, lower alkyl sulfonyl, aminocarbonyl, cyano and trifluoromethyl $m$ is zero or an integer from 1 to 5 with the proviso that when $X_1$ is a lower alkylene dioxy $m$ is 1 or 2 b. a bicyclic radical of the general formula

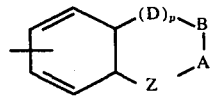

in which

1. Z and A together form an ethylidene radical, B and D together form an ethylidene radical and $p$ is 1

2. Z is an imino radical — NH — A and B together form an ethylidene radical, D is a methylene radical and $p$ is zero, 1 or 2

3. Z is a sulphur atom, A and B together form an ethylene or an ethylidene radical, D is a methylene radical and $p$ is zero or an integer from 1 to 3

The invention also provides acid addition salts of the compounds of the general formula I Due to their basic character, mineral or organic acids may be added to the compounds of general formula I. Such acids are preferably therapeutically compatible mineral or organic acids and there are mentioned as example of preferred salts, those with hydrobromic acid, sulphuric acid, phosphoric acid, acetic acid, propionic acid, maleic acid, fumaric acid, methylsulphonic acid, isethionic acid, glucose-1 phosphoric acid and hydrochloric acid.

Among the compounds of general formula I they are presently preferred the aryloxy lower alkyl piperidines of the general formula I'.

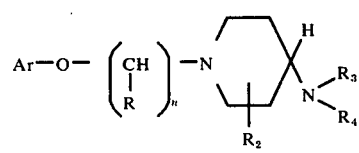

(I)

in which

R is a hydrogen atom or a lower alkyl radical,
n is an integer from 2 to 4,
$R_2$ is a hydrogen atom or a lower alkyl radical,
$R_3$ is the acyl radical of an alkane carboxylic acid having up to 10 carbon atoms,
$R_4$ is a phenyl radical, and
Ar is
a. a phenyl radical of the general formula

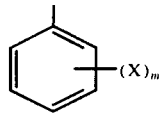

in which X is a substituent selected from halogen atoms and lower alkyl, lower alkenyloxy, lower alkynyloxy, lower alkylthio, carboxyl, lower alkoxycarbonyl, nitro, amino, lower alkyl amino, di (lower alkyl) amino, lower acylamino, sulfamido, lower alkylaminosulfonyl, (di lower alkyl amino) sulfonyl, lower alkylsulfonyl, amino carbonyl, cyano and trifluoromethyl radicals, and m is zero or an integer from 1 to 5, or
b. a homo -or heterobicyclic radical of general formula

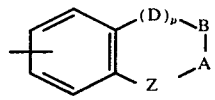

in which
i. Z and A together form an ethylidene radical, B and D together form an ethylidene radical and p is 1; or
ii. Z is an imino radical — NH —, A and B together form an ethylidene radical, D is a methylene radical and p is zero, 1 or 2; or
iii. Z is a sulphur atom, A and B together form an ethylene radical or an ethylidene radical, D is a methylene radical and p is zero or an integer from 1 to 3, and the acid addition salts thereof.

The term "lower alkyl" is used herein to designate a hydrocarbyl group having from 1 to 6 carbon atoms in a straight or branched chain and which may be substituted by a hydroxyl, lower alkoxy or dilower alkyl amino group. Examples of such lower alkyl groups are methyl, ethyl, isopropyl, sec butyl, neo-pentyl, tert.butyl, n-hexyl, hydroxyethyl and diethylaminoethyl groups.

The term "halogen" is used herein to designate preferably fluorine or chlorine atoms. It may be, also, bromine or iodine The term "lower alkenyl" is used herein to designate a hydrocarbyl group with one or more olefinic double bonds and having from 2 to 10 carbon atoms in a straight or branched chain. Examples of such alkenyl groups are allyl, methallyl, isopentenyl, dimethyl allyl, butenyl and triallyl methyl group.

The term "lower alkynyl" is used herein to designate a hydrocarbyl group having a triple bond and having from 2 to 6 carbon atoms, for example, the ethynyl, propynl-yl, propyn-2-yl and methyl-1 but-2-ynyl groups.

Preferred acyl radicals are especially those derived from lower alkanoic acids, for example acetic acid, butyric acid, isovalerianic acid, caproic acid, diethyl-amino acetic acid, pimelic acid, succinic acid, β-ethoxy-acetic acid and (di n-propyl) acetic acid.

The term "lower alkoxy" is used therein to designate a lower alkyloxy radical having from 1 to 6 carbon atoms and which may be substituted in the alkyl chain by a hydroxy, a, acyloxy or a dilower alkylamino radical.

The term "lower alkylene dioxy" is intended to designate a methylene dioxy radical, an ethylene dioxy or a propylene dioxy radical.

When X is substituted with at least a lower alkyl radical, the carbon atom which bears this substituent is asymmetric; such compounds of general formula I may be resolved into their stereoisomers and the compounds of the present invention can therefore be in racemic or optically-active forms.

In addition, when $R_2$ is a lower alkyl radical, a new center of symmetry is created and the diastereoisomers may be resolved. The amino side chain in the piperidine ring also produces an asymmetric carbon atom. The corresponding diastereoisomers may be separated by resolution by chemical or physical methods.

The compounds of the present invention possess interesting pharmacological properties, especially antihypertensive properties. Their pharmacological properties are distinct from those of 4-aminopiperidines previously described in the literature (Brevets speciaux de Medicament N° 2429 M, 2430 M and 2431 M) as having potent analgesic and neuroleptic properties. The compounds of the general formula I are devoid of any significant analgesic properties. The compounds of the present invention may therefore be used for therapeutic use in human or veterinary medicine, as drugs for treating hypertension without risk of noxious side-effects.

Due to their interesting pharmacological properties the following compounds may particularly be cited:
- N-(2,6 dichlorophenoxy) ethyl 4-(N'-phenyl N'-propionylamino) piperidine
- N-(2,6-dimethyl phenoxyethyl) 4-(N'-phenyl N'-propionylamino) piperidine
- N-(2,6-dimethoxy phenoxyethyl) 4-(N'-phenyl N'λ propionylamino) piperidine
- N-(2,6-dimethyl phenoxypropyl) 4-(N'-phenyl N'λ propionylamino) piperidine
- N-(α-naphtoxyethyl) 4-(N'-phenyl N'propionylamino) piperidine
- N-[2-(2,6-dimethyl phenoxy) propyl]4-N'-phenyl N'-propionylamino) piperidine
- N-(2,6-dimethyl phenoxyethyl) 4-[N'phenyl N'(dipropyl acetylamino)] piperidine
- N-(2,6-dimethyl phenoxyethyl) 4-[N'(3,4-methylene dioxyphenyl)N'propionylamino] piperidine
- cis dl N-(2,6 dimethyl phenoxyethyl) 3-methyl 4-(N'-phenyl N'-propionylamino) piperidine For therapeutic use, they can be administered in the form of pharmaceutical compositions including a compound of general formula I as active ingredient and one or more non-toxic inert pharmaceutical carriers suitable for oral, parenteral, sublingual or rectal administration.

More specifically, the pharmaceutical compositions may be in the form of ampuls, phials, multidose flasks, autoinjectable syringes, tablets, coated tablets, capsules, powders, granules, syrups, sublingual tablets and suppositories.

The useful posology will vary depending on the therapeutic use, the age and the weight of the patient and the seriousness of the illness. It may range from 1 to 250 mg per unit dosage and the administration may be repeated one to four times a day.

The present invention also provides a process for producing compounds of general formula I which comprises reacting a 4-aminopiperidine of general formula III

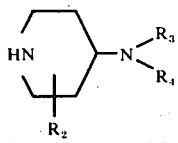

(III)

in which $R_2$, $R_3$ and $R_4$ have meanings given above with an ester of an aryloxy alkanol of the general formula II

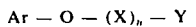

Ar — O — (X)$_n$ — Y            (II)

in which Ar —, X, n have the same meanings given above, and Y is a halogen atom or the acyl residue of an alkylsulphonic acid or an arylsulphonic acid, to obtain a compound of general formula I which may, if desired, be salified by addition of a mineral or organic acid or resolved into its optical isomers or diastereoisomers.

According to the present invention, the above-described condensation is preferably carried out in an inert solvent in the presence or absence of a basic agent. Preferably the solvent is a polar solvent, such as dimethylformamide, dimethylacetamide, hexamethylphosphoramide or acetonitrile. The solvent may also be a halogenated solvent such as methylene chloride or dichloroethane, an aromatic hydrocarbon such as benzene or toluene, or a cycloalkane such as cyclohexane.

Preferred esters are those which are derived from readily cleaved acids such as methanesulphonic acid, ethanesulphonic acid, benzenesulfonic acid or p-toluenesulphonic acid. Among the halides, chlorides and bromides are especially referred. When a bromide is used, it is especially suitable to carry out the condensation in the presence of an alkali metal iodide, in the presence of a dilower alkyl ketone such as acetone or methylisobutyl ketone.

The basic agent may be a trilower alkylamine such as triethylamine, a dilower alkyl arylamine such as dimethylamino aniline or a pyridine base such as pyridine, collidine or lutidine.

The basic agent may also be an excess of aminopiperidine of general formula III or the solvent when it is a disubstituted lower alkylamide or a phosphoramide.

The present invention also provides a process for producing compounds of general formula I which comprise submitting a compound of general formula IV

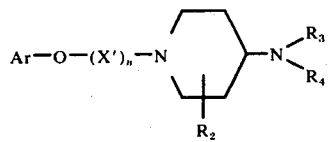

(IV)

in which n, Ar, $R_2$, $R_3$ and $R_4$ have the meanings given above, and X' is a radical selected from the group consisting of — $CH_2$ — CHOH, — CHOH — $CH_2$ —, — CO — $CH_2$ — and $CH_2$ — CO— to the action of a reducing agent and recovering the desired compound of general formula I Preferably the reducing agent is hydrogen in the presence of a catalyst such as platinum or palladium. The reducing agent is hydrazine in the presence of potassium hydroxide when an oxo group is present in the alkylene chain.

According to another aspect of the invention, there is provided a process for producing a compound of general formula I which comprises condensing compound of general formula II

Ar — O — (X)$_n$ — Y            (II)

in which Ar, X, Y and n have the above-given definitions with a 4-aminopyridine of the formula VI

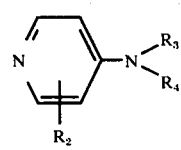

(VI)

in which $R_2$, $R_3$ and $R_4$ have the meanings give above, to produce a 4-amino pyridinium salt of the formula VII

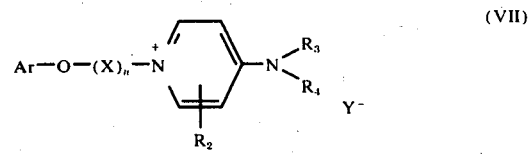

(VII)

on which the substituents are defined as above specified and reducing the latter by catalytic hydrogenation or by means of mixed alkali metal hydride to an amino piperidine of formula I.

The catalyst may be based on a metal of the platinium family such as platinum, palladium, iridium or rhodium.

The mixed metal hydride may be an alkali metal borohydride or an alkali metal aluminohydride.

A compound of general formula I may also be produced according to the invention by condensing an aryloxy radical of general formula VIII

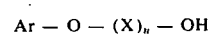

Ar — O — (X)$_n$ — OH            (VIII)

in which Ar, X and n have the above-specified meanings with an aminopiperidine of general formula II

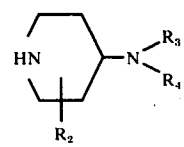

(II)

in which $R_2$, $R_3$ and $R_4$ have the meanings given above, in the presence of a hydrogenation catalyst to produce the desired compound of formula I. More specifically the hydrogenation catalyst is RANEY nickel and, preferably RANEY nickel WR.

The compounds of general formula I may further be produced according to the invention by submitting an aryloxy alkylpiperidine of the formula V

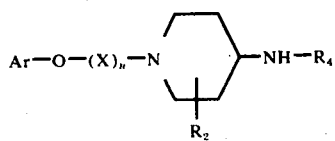

in which Ar, X, $n$, $R_2$ and $R_4$ are defined as above to the action of an acylating agent derived from an alkane carboxylic acid having up to 10 carbon atoms and recovering the desired compound of formula I.

The acylating agent is preferably a halide of the alkane carboxylic acid or the alkane carboxylic acid in the presence of a dehydrating agent such as a dialkyl-or a dicycloalkyl carbodiimide.

The compounds of general formula I may also be produced according to the invention by submitting an aminopiperidine of general formula II

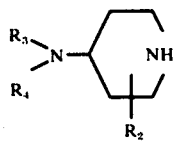

in which $R_2$, $R_3$ and $R_4$ have the meanings given above to the action of an alkylene difunctional derivative of the formula IX $$Y - (X)_n - OH \qquad (IX)$$

in which R, $n$ and Y have the meanings given above to obtain an (aminopiperidino) alkanol of the formula X

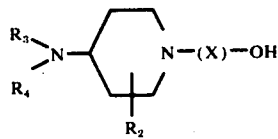

treating the latter with an acylating agent derived from a hydrohalic acid, to produce a halide of the formula XI

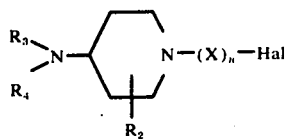

in which Hal is a halogen atom, and reacting the halide with a phenol of the formula XII $$Ar - OH \qquad (XII)$$

in which Ar has the meaning given above to produce a compound of general formula I.

Preferably the acylating agent derived from a hydrohalic acid is phosphorus tribromide, phosphorous sxychloride, a sulphuric or sulphonyl halide, such as thionyl chloride or sulphuryl chloride, an aryl sulphonyl halide such as benzene sulphonyl chloride or p-toluenesulphonyl chloride or a metallic halide such as vanadium chloride.

The optically-active reagent which may be used for resolving the compounds of formula I is preferably an optically-active organic acid such an optically-active carboxylic acid, for example d-tartaric acid, 1-ketogulonic acid, 1-ascorbic acid, 1-menthyloxyacetic acid, abietic acid, d-N,N-diemthyl tartramic acid, an optically-active sulphonic acid for example d-camphosulphonic acid or an optically-active phosphoric acid such as d-glucose-1-phosphoric acid or d-glucose-1,6-diphosphoric acid.

The starting materials of general formula III and the starting materials of general formula VIII may be obtained according to the processes described in U.S. Patent No. 3,131,218 and in J. Med. Chem. 6 (1963) 63. The starting materials of general formula II may be obtained according to known processes, for example that disclosed in German Patent No. 1,470,357.

The following Examples illustrate the invention. The temperatures are expressed in degrees Centigrade.

EXAMPLE 1

N-(2,6 dichlorophenoxy)-ethyl-4-(N'phenyl-N'-propionylamino)piperidine

Step A (2,6-dichlorophenoxy-ethyl) bromide 7.5 g dichlorophenol are dissolved in 600 ml ethanol and added to a solution of 10.4 g sodium in 250 ml ethanol at room temperature. There is then added 187 g ethylene dibromide and the resulting mixture is refluxed for 7 hours. After return to ambient temperature, the reaction mixture is concentrated under reduced pressure producing an oily residue. The latter is suspended in water and extracted three times with ether. The organic phases are combined, washed many times with 5 N sodium hydroxide solution and then with water until the washings are neutral. The organic solution is then dried and the solvent is distilled off. The residue obtained is a liquid weighing 100.8 g (theory 120 g). It is purified by fractional distillation. The pure (2,6-dichloro-phenoxy ethyl) bromide distills at 98°–100° under 0.05 mm Hg. 74.9 g of pure product is obtained i.e. a yield of 62%. (2,6 dichlorophenoxy ethyl) bromide has been described in U.S. Pat. No. 3,209,023 with a boiling point of 157°–160° under 11 mm Hg.

Step B

N-(2,6 dichlorophenoxy)-ethyl-4-(N'-phenyl-N'-propionylamino)piperidine

To 8.2 g of 4-(N'-phenyl-N'-propionyl) aminopiperidine dissolved in methyl isobutyl ketone are added 11.2 g sodium carbonate, a few milligrams of potassium iodide and 9.45 g (2,6-dichlorophenoxy-ethyl) bromide. The whole mixture is refluxed for 27 hours. The mixture is then allowed to cool to room temperature, filtered and evaporated to dryness under reduced pressure. 14.2 g of N-2,6-dichlorophenoxy)-ethyl-4-(N'-phenyl N'-propionylamino)-piperidine are thus recovered as an oily product which crystallized quickly. The crude product is purified by recrystallization from 80 ml hot cyclohexane. At ambient temperature crystallization begins and after one hour, the crystalline product is filtered, washed with cold cyclohexane and dried at 60°. 11.8 g of pure product are obtained, melting at 103° (yield 80%). Further recrystallization does not alter the melting point. The product can be converted into its methane sulfonic acid addition salt. This salt is soluble in water.

EXAMPLE II

N-(2,6-dimethylphenoxyethyl)-4-(N'-phenyl-N'-propionylamino)piperidine

Step A (2,6-dimethylphenoxyethyl) bromide

Using the procedure described in Example I step A and starting from 53 g 2,6-dimethylphenol, 13.4 g (2,6-dimethylphenoxyethyl) bromide are obtained as a liquid boiling at 135°–138° under 20 mm Hg.

Step B

N-(2,6-dimethylphenoxyethyl)-4-(N'-phenyl-N'-propionylamino)piperidine

Using the procedure described in Example I and starting from 12.7 g (2,6-dimethylphenoxyethyl) bromide and 12.8 g 4-(N'-phenyl-N'-propionylamino)-piperidine, 16.1 g of the title product are obtained melting at 82° after recrystallization from hexane. Mixing the compound with 4-(N'-phenyl-N'-propionylamino)-piperidine depresses the melting point.

EXAMPLE III

N-(2,6-dimethoxyphenoxyethyl)-4-(N'-phenyl-N'-propionylamino)piperidine

Step A (2,6-dimethoxyphenoxyethyl) bromide

From 33.5 g pyrogallol 2,6-dimethylether, 12.1 g of (2,6-dimethoxyphenoxyethyl) bromide are obtained as a liquid boiling at 128°–131° under 0.04 mm Hg.

The same product has been described by Drain J. Med. Chem. 6 (1963) 63 with a boiling point of 92° under 0.04 mm Hg.

Step B

N-(2,6-dimethoxyphenoxyethyl)-4-(N'-phenyl N'-propionylamino)piperidine

Using the procedure in Example I step B and starting from 12.1 g (2,6 dimethoxyphenoxyethyl) bromide and 10.7 g 4-(N'-phenyl-N'-propionylamino)-piperidine, 15 g N-(2,6-dimethoxyphenoxyethyl)-4-(N'-phenyl-N'-propionylamino)piperidine are recovered after crystallization from cyclohexane, melting at 71°–72°.

EXAMPLE IV

N-(2,6-dimethylphenoxypropyl)-4-(N'-phenyl-N'-propionylamino) piperidine

Step A

Using the procedure described in Example I step A and starting from 48.8 g of 2,6-dimethylphenol and 100.95 g 1,3-dibromopropane, 24.7 g of (2,6-dimethylphenoxypropyl) bromide are obtained boiling from 94° to 99° under 0.05 mm Hg.

Step B

Using the procedure described in Example I step B and starting from 14.7 g of 4-(N'-phenyl-N'-propionylamino)-piperidine and 15.51 g of (2,6-dimethylphenoxy propyl) bromide, 27 g crude N-(2,6-dimethylphenoxypropyl)-4-(N'-phenyl-N'-propionylamino)-piperidine are obtained as white crystals insoluble in the usual solvents.

The crude product is purified by converting it into its hydrochloride and then liberating the free base by alkalinization. After drying, 17.3 g of the free base are recovered. The product is further purified by recrystallization from hot hexane. A first crop weighing 11.6 g is obtained i.e. a yield of 45%. Its melting point is 80°–82°.

EXAMPLE V

N-(3-trifluoromethylphenoxyethyl)-4-(N'-phenyl-N'-propionylamino)-piperidine

Step A

Using the procedure described in Example I step A and starting from 69 g 3-trifluoromethylphenol, 65 g of crude (3-trifluoromethylphenoxyethyl) bromide are obtained which are further purified by fractional distillation. The pure fraction boils at 122°–126° under 10 mm Hg (yield 26%).

Step B

Using the procedure described in Example I step B and starting from 9.85 g (3-trifluoromethylphenoxyethyl) bromide, 16 g of crude N-(3-trifluoromethylphenoxyethyl)-4-(N'-phenyl-N'-propionylamino)-piperidine are obtained after 24 hours heating under reflux. The crystalline product is converted for purification to its methane sulphonic acid addition salt. This salt melts at 140° then about 190°.

The methane sulphonate is transformed into the free base by adding sodium hydroxide. 7 g of pure N-(3-trifluoromethylphenoxyethyl) 4-(N'-phenyl-N'-propionylamino)-piperidine are thus obtained which may also be converted into its hydrochloride. The latter is soluble in water.

EXAMPLE VI

N-phenoxyethyl-4-N'-phenyl-N'-propionylamino)-piperidine

By condensing 14.7 g 4-(N'-phenyl-N'-propionylamino)-piperidine and 19.9 g phenoxyethyl chloride, they are obtained after 24 hours reflux 22 g of the title product which after recrystallization from hot cyclohexane gives a first crop weighing 13.5 g. The pure compound melts at 100°–102°. It is soluble in hydrochloric acid. The solution after distillation leads to the recovery of the hydrochloride. The hydrochloride is soluble in water.

EXAMPLE VII

N-(2-cyanophenoxyethyl)-4-(N'-phenyl-N'-propionylamino)-piperidine

Step A

Using the procedure described in Example I step A and starting from O-cyanophenol (25.8 g) they are obtained after purification and distillation 16.7 g of (2-cyanophenoxy) ethyl bromide boiling at 128°–130° under 0.03 mm Hg. The yield amounts to 33% of the theory.

Step B

Using the procedure described in Example I step B and starting from 13.5 g 4-(N'-phenyl-N'-propionylamino)-piperidine and 13 g (2-cyanophenoxy) ethyl bromide, 18.9 N-(2-cyanophenoxyethyl)-4-(N'-phenyl-N'-propionylamino)-piperidine are recovered. The product is further purified by recrystallization from isopropyl acetate. 15.6 g of pure product are obtained as white crystals which melt at 90°. The yield amounts to 66.5%.

EXAMPLE VIII

N-(2-methylphenoxyethyl)-4-(N'-phenyl-N'-propionylamino)-piperidine

Step A

Using the procedure described in Example I and starting from 47 g o-cresol and 187 g dibromoethane, 27 g of (2-methylphenoxyethyl) bromide are obtained. The product is purified by distillation. It boils at 132°–134° under 20 mm Hg (yield 13.3 g).

Step B

Using the procedure described in Example I step B and starting from 14.4 g of 4-(N'-phenyl-N'-propionylamino)-piperidine and 13.3 g of (2-methylphenoxyethyl) bromide, 22.6 g of N-(2-methylphenoxyethyl)-4-(N'-phenyl-N'-propionyl-amino)-piperidine are produced.

This product is purified by dissolving it in 4 N hydrochloric acid solution, filtering the acid solution of hydrochloride and alkalinizing it with sodium hydroxide while cooling. The free base is further extracted with ether, the organic phases are combined, washed with water, dried and the ether distilled off. The oily residue weighing 20.9 g is recrystallized from hexane providing 14.3 g of a first crop melting at 66° (56% yield).

EXAMPLE IX

N-(2-allylphenoxyethyl)-4-(N'-phenyl-N'-propionylamino)-piperidine

Step A (2-allylphenoxyethyl) bromide

Using the procedure described in Example I step A and starting from 43.5 g o-allylphenol and 140 g dibromoethane, 35 g of crude product are produced which after distillation under reduced pressure give 14 g of pure compound. The latter boils at 150°–154° under 18–20 mm Hg.

Step B

Using the procedure described in Example I step B and starting from 14 g of (2-allylphenoxyethyl) bromide, there are produced 22.2 g of N-(2-allylphenoxyethyl)-4-(N'-phenyl-N'-propionylamino)-piperidine. After recrystallization from hot cyclohexane, 14.1 g of pure compound are recovered which melts at 66°–68°. The yield amounts to 62%.

EXAMPLE X

Using the procedure of Example I step B and starting from (α-naphtoxyethyl) bromide and 4(N-phenyl N-propionylamino) piperidine, N(α-naphtoxyethyl) 4-(N'-phenyl-N'-propionylamino) piperidine is obtained melting at 110°–112° (cyclohexane)

EXAMPLE XI

Using the procedure of Example I step B and starting from (p.fluorophenoxyethyl) bromide and 4-(N-phenyl N-propionylamino) piperidine, N(p.fluorophenoxyethyl) 4(N'-phenyl N'-propionylamino) piperidine is obtained melting at 93°–94°.

EXAMPLE XII

Using the procedure of Example I step B and starting from 2-(2,6-dimethylphenoxy) propyl bromide and 4-(N-phenyl N-propionylamino) piperidine N[2-(2,6-dimethylphenoxy) propyl] 4-(N-phenyl N-propionylamino) piperidine which melts at 78°.

EXAMPLE XIII

Using the procedure of Example I step B and starting from (4-acetamidophenoxyethyl) bromide and 4-(N-phenyl N-propionylamino) piperidine, N-[(4-acetamidophenoxy) ethyl] 4-(N'-phenyl N'-propionylamino) piperidine is obtained which melts at 78°.

EXAMPLE XIV

Using the procedure of Example I step B and starting from (8-thiachromanyloxyethyl) bromide and 4-(N-phenyl N-propionylamino) piperidine, N (8-thiachromanyloxyethyl) 4-(N'-phenyl N'-propionylamino) piperidine is obtained and isolated as its oxalate which melts at 182°–184°.

EXAMPLE XV

Using the same procedure the following compounds have been obtained

EXAMPLE XV

| Using the same procedure the following compounds have been obtained | |
|---|---|
| Starting material | Final product |
| (2,6-di isopropylphenoxy) ethyl bromide | N-[2,6-diosopropylphenoxy) ethyl] 4-(N'-phenyl N'-propionylamino) piperidine MP=73° (petroleum ether) |
| (2,6-di sec butylphenoxy) ethyl bromide | N-[2,6-di secbutylphenoxy) ethyl] 4-(N'-phenyl N'propionylamino) piperidine isolated as its hydrochloride MP=120° (water) |
| (2,4,6-trimethylphenoxy) ethyl bromide | N-[(2,4,6-trimethylphenoxy) ethyl] 4-(N'-phenyl N'-propionylamino-piperidine MP=84° (petroleum ether) |
| (2-allyloxyphenoxy) ethyl bromide | N-[(2-allyloxyphenoxy) ethyl] 4-(N'-phenyl N'-propionylamino) piperidine MP = 148–150 of its acid oxalate |
| (2,6-diethylphenoxy) ethyl bromide | N-[(2,6-diethylphenoxy) ethyl] 4-(N'-phenyl N'-propionylamino) piperidine MP = 180 of its methane sulfonic salt |
| (2,6-dimethyl 4-nitrophenoxy) ethyl bromide | N-[(2,6-dimethyl 4-nitrophenoxy) ethyl] 4-(N'phenyl N'-propionyl-amino) piperidine MP = 120 (cyclohexane) |
| (2-methyl 6-allylphenoxy) | N-[(2-methyl 6-allylphenoxy) ethyl] 4-(N'-phenyl N'-propionylamino) pi- |

EXAMPLE XV-continued

Using the same procedure the following compounds have been obtained

| Starting material | Final product |
|---|---|
| ethyl bromide | peridine MP = 50–52°. This compound is soluble in dilute solution of methane sulphonic acid. |
| (2,6-dimethylphenoxy) ethyl bromide and 4-(N-phenyl N-acetylamino) piperidine | N-[(2,6-dimethylphenoxy) ethyl] 4-N'-phenyl N'-acetylamino) piperidine MP = 134°. This compound is soluble in N/10 solution of hydrochloric acid |
| (2-methoxycarbonyl 3-methyl 6-isopropylphenoxy) ethyl bromide | N-[(2-methoxycarbonyl 3-methyl 6-isopropylphenoxy) ethyl]4-(N'-phenyl N'-propionylamino) piperidine MP = 100–102° (cyclohexane) This compound is soluble in aqueous solution of methane sulphonic acid. |

EXAMPLE XVI

N-[(2,6-dimethyl 4-amino)phenoxy] 4-(N'-phenyl N'-propionylamino) piperidine and its dihydrochloride By catalytic hydrogenation in the presence of platinum of N[(2,6-dimethyl 4-nitrophenoxy) ethyl] 4-(N'-phenyl N'-propionylamino) piperidine, N-[(2,6-dimethyl 4-aminophenoxy) ethyl] 4-(N'-phenyl N'-propionylamino) piperidine is obtained and is isolated as its dihydrochloride by adding an excess of hydrochloric acid.

The dihydrochloride melts at 206°–210° C. It is freely soluble in water.

EXAMPLE XVII

N[(2,6-dimethylphenoxy) ethyl] 4-(N'-phenyl N'di-n propylacetylamino) piperidine and its acid oxalate Using the procedure of example I step B, (2,6-dimethylphenoxy) ethyl bromide is condensed with 4,4-ethylenedioxy piperidine and the resulting N-[(2,6-dimethylphenoxy) ethyl] 4,4-ethylenedioxy piperidine is hydrolysed into the corresponding 4-oxo piperidine by means of dilute hydrochloric acid. The N-[(2,6-dimethylphenoxy) ethyl] 4-oxo piperidine is condensed with aniline in the presence of p. toluene sulfonic acid giving N-[(2,6-dimethylphenoxy) ethyl] 4-phenylimino piperidine The latter is reduced into N-[(2,6-dimethylphenoxy) ethyl] 4-phenylamino piperidine by means of sodium borohydride in methanol. (melting point 64°)

N-[(2,6-dimethylphenoxy) ethyl] 4-phenylamino piperidine is reacted with dipropylacetyl anhydride giving N-[(2,6-dimethylphenoxy) ethyl] 4-(N'phenyl N'dipropylacetylamino) piperidine whose acid oxalate melts at 203°.

Similarly using para-toluidine instead of aniline, N[2,6-dimethylphenoxy) ethyl] 4-(N'-p. methyl phenyl N'-propionylamino) piperidine is obtained (MP=91°).

Similarly using para-anisidine instead of aniline N-[(2,6-dimethylphenoxy) ethyl] 4-(N'p. methoxy phenyl N'-propionylamino) piperidine is obtained (MP=65°–66°).

Similarly using 3,4-diethylenedioxy aniline, instead of aniline, N-[(2,6-dimethylphenoxy ethyl] 4-[N'-(3,4-methylene dioxy phenyl) N'-propionylamino] piperidine is obtained MP of its acid oxalate F=216°–218°.

Similarly using 3,4, 5-trimethoxy aniline instead of aniline, N-[(2,6-dimethylphenoxy ethyl] 4-[N'-(3,4,5-trimethoxyphenyl N'-propionylamino] piperidine is obtained. Its acid oxalate melts at 202°.

EXAMPLE XVIII cis dl N-[(2,6-dimethylphenoxy) ethyl] 3-methyl 4-(N'-phenyl N'-propionylamino) piperidine.

Using the procedure of example I step A and starting from 3,25 g of 2,6-dimethylphenoxy ethyl and 2,7 g of cis dl 3-methyl 4-phenylamino piperidine, 4.9 g of cis dl N-[(2,6-dimethylphenoxy) ethyl] 3-methyl 4-phenylamino piperidine is obtained, and is immediately condensed with propionyl anhydride in toluenic medium. 5 g of cis dl N-[(2,6-dimethylphenoxy) ethyl] 3-methyl 4-(N'-phenyl N'-propionylamino) piperidine is obtained after recrystallization from n-pentane; MP=108°–109°.

EXAMPLE XIX

Pharmacological study of the compounds a. acute toxicity

The acute toxicity of the compounds of formula I has been determined on batches of mice (Swiss strain) weighing about 20 g. The compounds have been administered intraperitoneally at increasing dosis. After a period of observation of 8 days during which the deaths are numbered, the average lethal dose is graphically calculated. It ranges depending on the compound from 25 mg/kg and 200 mg/kg.

b. search of a neurological effect

In the mice the first active dosis on the Central Nervous System appears to be at 25 mg/kg by intraperitoneal way. At this dosis the motility of the mice is slightly decreased. At higher dosis the mice show a trembling walking and weak convulsive state.

On the contrary in the rat the reflexes and muscular tone are only slightly altered and in the dog the symptomatology is of no clear signifiance.

c. search of an analgetic effect

The compounds have been tested by the method of the hot plate as described by Haffner in the mice. The time of reaction is slightly increased by this effect appears not to be proportional to the injected dosis.

d. hypotensive effect

The compounds of formula I have been administered by intravenous way to batches of dogs, previously anesthetized with Nembutal at increasing dosis. The experienced dosis ranges from 1 to 5 mg/kg. The compounds of formula I induced both a decrease of the mean arterial pressure of 20 to 40% and a decrease of the cardiac rythm of 30 to 40%. The duration of the hypotensive effect is interesting and extend from 20 to 45 mn depending on the injected dosis.

What we claim is:

1. The aryloxy lower alkyl piperidines selected from the group consisting of

-N-(2,6 dichlorophenoxy) ethyl 4-(N'-phenyl N'-propionylamino) piperidine;

-N-(2,6-dimethyl phenoxyethyl) 4-N'-phenyl N'-propionylamino) piperidine;

-N-(2,6-dimethoxy phenoxyethyl) 4-(N'-phenyl N'-propionylamino) piperidine;

-N-(2,6-dimethyl phenoxypropyl) 4-(N'-phenyl N'-propionylamino) piperidine;

-N-[2-(2,6-dimethyl phenoxy) propyl] 4-N'-phenyl N'-propionylamino piperidine;

-N-(2,6-dimethyl phenoxyethyl) 4-[N'-phenyl N'-(dipropylacetylamino)] piperidine;

-N-(2,6-dimethyl phenoxyethyl) 4-[N'(3,4-methylene dioxyphenyl) N'-propionylamino] piperidine;

-cis dl N-(2,6 dimethyl phenoxyethyl) 3-methyl 4-(N'-phenyl N'-propionylamino) piperidine;

and addition salts thereof.

2. -N-(2,6 dichloropenoxy) ethyl 4-(N'-phenyl N'-propionylamino) piperidine according to claim 1.

3. -N-(2,6-dimethyl phenoxyethyl) 4-(N'-phenyl N'-propionylamino) piperidine according to claim 1.

4. -N-(2,6-dimethoxy phenoxyethyl) 4-(N'-phenyl N'-propionylamino) piperidine according to claim 1.

5. -N-(2,6-dimethyl phenoxypropyl) 4-(N'-phenyl N'-propionylamino) piperidine according to claim 1.

6. -N-[2-(2,6-dimethyl phenoxy) propyl] 4-N'-phenyl N'-propionylamino) piperidine according to claim 1.

7. -N-(2,6-dimethyl phenoxyethyl) 4-[N'-phenyl N'-(dipropyl acetylamino)] piperidine according to claim 1.

8. -N-(2,6-dimethyl phenoxyethyl) 4-[N'(3,4-methylene dioxyphenyl) N'-propionylamino] piperidine according to claim 1.

9. - cis dl N-(2,6 dimethyl phenoxyethyl) 3-methyl 4-(N'-phenyl N'-propionylamino) piperidine according to claim 1.

10. The pharmaceutical compositions useful in the treatment of hypertension including a compound of claim 1 as active ingredient and one or more non-toxic inert pharmaceutical carriers suitable for oral, parenteral, sublingual or rectal administration.

11. A pharmaceutical composition according to claim 10 in the form of ampuls, phials, multidose flasks, autoinjectable syringes, tablets, coated tablets, capsules, powders, granules, syrups, sublingual tablets and suppositories.

12. A pharmaceutical composition according to claim 10 containing from 1 to 250 mg of a compound of claim 1 as active ingredient per unit dosage.

13. A method for treating hypertensive patients which comprises administering to humans or animals suffering said illness a safe but efficient amount of a compound of claim 1.

14. The method of claim 13 in which the safe but efficient amount of a compound of claim 1 ranges from 1 to 1000 mg per day.

* * * * *

UNITED STATES PATENT OFFICE
CERTIFICATE OF CORRECTION

Patent No. 4,027,028          Dated May 31, 1977

Inventor(s) Michel Vincent et al

It is certified that error appears in the above-identified patent and that said Letters Patent are hereby corrected as shown below:

Col. 4, line 42-43; "4-(N'-phenyl N' λ propiony-lamino)" should read -- 4-(N'-phenyl N' propiony-lamino)--
Col. 4, line 44-45; "4-(N'-phenyl N' λ propiony-lamino)" should read -- 4-(N'-phenyl N' propiony-lamino)--
Col. 5, line 53-54; "comprise" should read --comprises--
Col. 7, line 68; "such an" should read --such as an--
Col. 8, line 20-21; "-propionylamino)piperidine" should read -- -propionylamino)-piperidine--
Col. 8, line 49-50; " -propionylamino)piperidine" should read -- -propionylamino)-piperidine--
Col. 9, line 5-6; " - propionylamino)piperidine" should read -- -propionylamino)-piperidine--
Col. 9, line 16-17; "-propionylamino)piperidine" should read -- -propionylamino)-piperidine--
Col. 9, line 26-27; "-propionylamino)piperidine" should read -- -propionylamino)-piperidine--
Col. 9, line 40-41; "-propionylamino)piperidien" should read -- -propionylamino)-piperidine--

UNITED STATES PATENT OFFICE
CERTIFICATE OF CORRECTION

Patent No. 4,027,028  Dated May 31, 1977

Inventor(s) Michel Vincent et al

It is certified that error appears in the above-identified patent and that said Letters Patent are hereby corrected as shown below:

Col. 9, line 47; "-propionylamino)piperidine" should read -- -propionylamino)-piperidine--

Col. 10, line 37; "4-N'-phenyl-N'-propiony-alamino)-" should read -- 4-(N'-phenyl-N'-propionylamino)- --

Col. 16, line 4-5; "N'(-dipropyl" should read -- N'(dipropyl --

Col. 16, line 26; "A method for treating hypertensive patients" should read -- A method for treating hypertension in hypertensive patients--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks